United States Patent
Steigauf et al.

(10) Patent No.: US 10,198,816 B2
(45) Date of Patent: Feb. 5, 2019

(54) MEDICAL EVALUATION MACHINE LEARNING WORKFLOWS AND PROCESSES

(71) Applicant: Virtual Radiologic Corporation, Minneapolis, MN (US)

(72) Inventors: Wade J. Steigauf, Bloomington, MN (US); Benjamin Strong, Minneapolis, MN (US); Shannon Werb, Sunfish Lake, MN (US)

(73) Assignee: Virtual Radiologic Corporation, Minneapolis, MN (US)

(*) Notice: Subject to any disclaimer, the term of this patent is extended or adjusted under 35 U.S.C. 154(b) by 0 days.

(21) Appl. No.: 15/809,786

(22) Filed: Nov. 10, 2017

(65) Prior Publication Data
US 2018/0204325 A1    Jul. 19, 2018

Related U.S. Application Data

(63) Continuation of application No. 15/168,567, filed on May 31, 2016, now Pat. No. 9,846,938.
(Continued)

(51) Int. Cl.
*G06K 9/00* (2006.01)
*G06T 7/00* (2017.01)
(Continued)

(52) U.S. Cl.
CPC .......... *G06T 7/0014* (2013.01); *G06K 9/4623* (2013.01); *G06K 9/627* (2013.01);
(Continued)

(58) Field of Classification Search
USPC ....................................................... 382/128
See application file for complete search history.

(56) References Cited

U.S. PATENT DOCUMENTS

| 7,970,188 B2 | 6/2011 | Mahesh et al. |
| 9,846,938 B2 | 12/2017 | Steigauf et al. |

(Continued)

OTHER PUBLICATIONS

"vRad Reaches Milestone: Deep Learning Algorithm Successfully Identifies Potential Intracranial Hemorrhaging; Operational Implementation Pending Regulatory Approval", vRad, (Dec. 8, 2015), 3 pgs.*

(Continued)

*Primary Examiner* — Gregory F Cunningham
(74) *Attorney, Agent, or Firm* — Schwegman Lundberg & Woessner, P.A.

(57) ABSTRACT

Systems and methods for processing electronic imaging data obtained from medical imaging procedures are disclosed herein. Some embodiments relate to data processing mechanisms for medical imaging and diagnostic workflows involving the use of machine learning techniques such as deep learning, artificial neural networks, and related algorithms that perform machine recognition of specific features and conditions in imaging data. In an example, a deep learning model is selected for automated image recognition of a particular medical condition on image data, and applied to the image data to recognize characteristics of the particular medical condition. Based on the characteristics recognized by the automated image recognition on the image data, an electronic workflow for performing a diagnostic evaluation of the medical imaging study may be modified, updated, or prioritized.

25 Claims, 9 Drawing Sheets

Related U.S. Application Data

(60) Provisional application No. 62/169,339, filed on Jun. 1, 2015.

(51) Int. Cl.
| | | |
|---|---|---|
| *G06K 9/62* | (2006.01) | |
| *G06K 9/46* | (2006.01) | |
| *G16H 30/40* | (2018.01) | |
| *G16H 40/20* | (2018.01) | |
| *G16H 50/20* | (2018.01) | |
| *G06N 99/00* | (2010.01) | |

(52) U.S. Cl.
CPC ......... *G06K 9/6257* (2013.01); *G06K 9/6263* (2013.01); *G16H 30/40* (2018.01); *G16H 40/20* (2018.01); *G06K 2209/05* (2013.01); *G06N 99/005* (2013.01); *G06T 2207/10081* (2013.01); *G06T 2207/10088* (2013.01); *G06T 2207/10116* (2013.01); *G06T 2207/20081* (2013.01); *G06T 2207/20084* (2013.01); *G16H 50/20* (2018.01)

(56) References Cited

U.S. PATENT DOCUMENTS

| | | |
|---|---|---|
| 2012/0243754 A1 | 9/2012 | Koff et al. |
| 2016/0015347 A1 | 1/2016 | Bregman-Amital et al. |
| 2016/0350919 A1 | 12/2016 | Steigauf et al. |

OTHER PUBLICATIONS

Deng, Li, et al., "Deep Learning Methods and Applications", Foundations and Trends in Signal Processing, vol. 7, No. 3-4, (2013), 197-387.*

"U.S. Appl. No. 15/168,567, Notice of Allowance dated Sep. 25, 2017", 10 pgs.

"Compassionate Allowances Conditions", Social Security, Retrieved from Internet on Sep. 18, 2017 Retrieved from URL: <https://www.ssa.gov/compassionateallowances/conditions.htm>, 1 pg.

"vRad and MetaMind Collaborate on Deep Learning Powered Workflows to Help Radiologists Accelerate Identification of Life-threatening Abnormalities", PRWeb, (Jun. 16, 2015), 3 pgs.

* cited by examiner

MEDICAL EVALUATION MACHINE LEARNING WORKFLOWS AND PROCESSES

PRIORITY

This application is a continuation and claims the benefit of priority to U.S. patent application Ser. No. 15/168,567, filed on May 31, 2016, which claims the benefit of U.S. Provisional Application Ser. No. 62/169,339, filed Jun. 1, 2015, both of which applications are incorporated by reference herein its entirety.

TECHNICAL FIELD

Embodiments pertain to techniques and systems for processing electronic data obtained from imaging or other diagnostic and evaluative medical procedures. Some embodiments relate to data processing mechanisms for medical imaging and diagnostic workflows involving the use of machine learning techniques such as deep learning, artificial neural networks, and related algorithms that perform machine recognition of specific features and conditions in imaging and other medical data.

DETAILED DESCRIPTION

Figure 1:
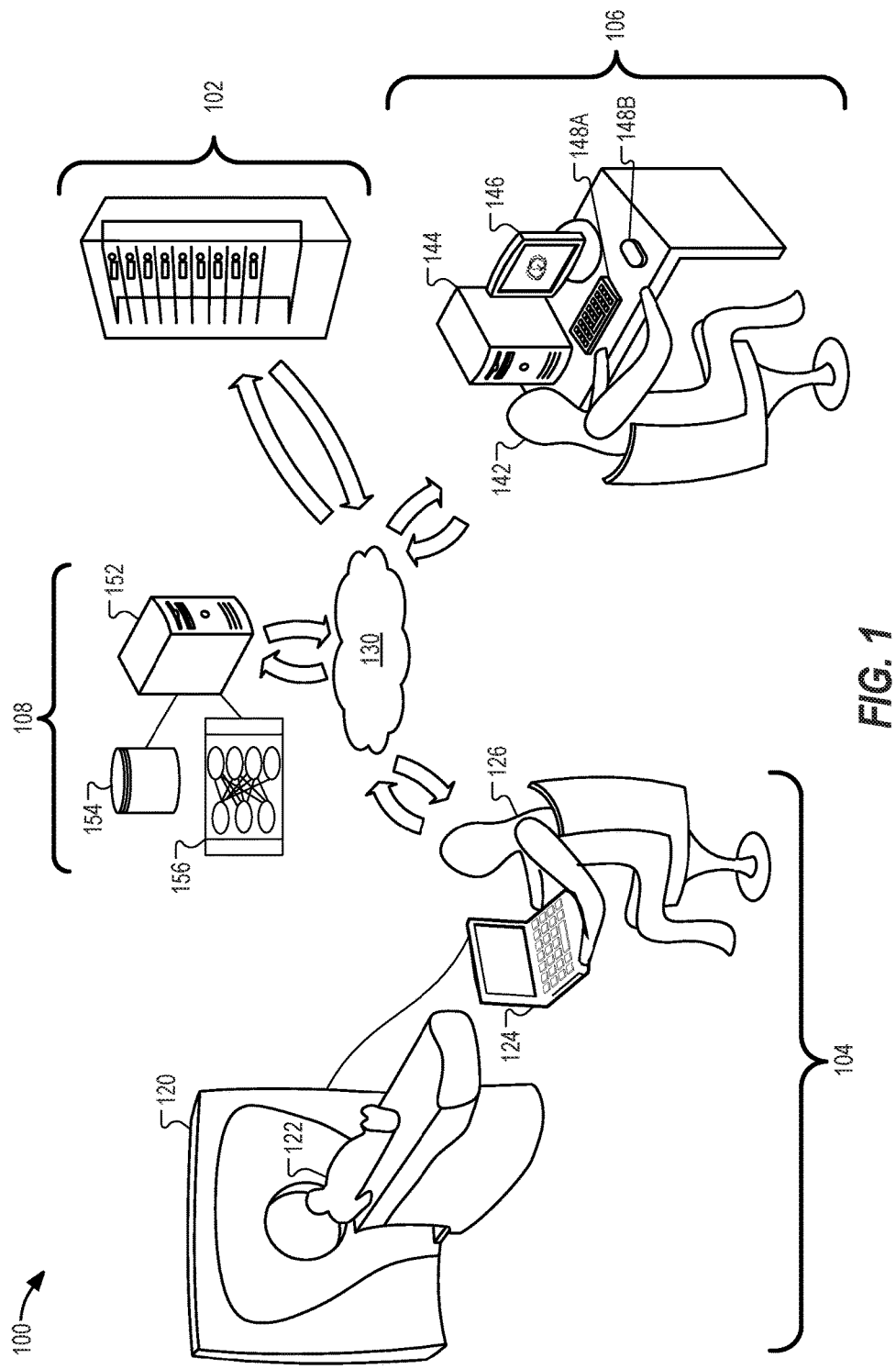
FIG. 1 illustrates a system configuration enabled for processing, coordinating, and directing medical imaging data in connection with a machine learning workflow according to an example described herein.

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments.

The present disclosure illustrates various techniques and configurations that enable the integration and use of machine learning analysis in a data-driven image evaluation workflow. For example, machine learning analysis (such as trained models of image detection of certain medical conditions) may be performed upon medical imaging procedure data produced as part of a medical imaging study. The medical imaging procedure data may include image data captured by an imaging modality, and order data (such as data indicating a request for a radiological image read), each produced to facilitate a medical imaging evaluation (such as a radiology read to be performed by a radiologist or a diagnostic evaluation by another qualified medical professional).

For example, the machine learning analysis may receive and process images from medical imaging procedure data, to identify trained structures, conditions, and conditions within images of a particular study. The machine learning analysis may result in the automated detection, indication, or confirmation of certain medical conditions within the images, such as the detection of urgent or life-critical medical conditions, clinically serious abnormalities, and other key findings. Based on the result of the machine learning analysis, the medical evaluation workflow for the images and the associated imaging procedure may be prioritized, or otherwise changed or modified. Further, the detection of the medical conditions may be used to assist the assignment of the medical imaging data to particular evaluators, the evaluation process for the medical imaging data, or implement other actions prior to, or concurrent with, the medical imaging evaluation (or the generation of a data item such as a report from such medical imaging evaluation).

The evaluation workflow activities which may be modified in connection with the techniques described herein, may include activities for a study having images that indicate a critical, urgent, or time-sensitive medical condition, such as: prioritizing the study in an electronic worklist of an evaluating user; re-assigning the study to a specialist who is proficient in diagnosing the critical medical condition; alerting a transmitting medical facility, an operations center, or one or multiple medical evaluators regarding the criticality of the study; identifying or labeling specific image locations in the study output based on the conditions identified in the study; and rearranging or reorganizing display characteristics of images or reporting data for the study based on the conditions identified in the study. These steps may be implemented by electronic (e.g., computer-implemented) operations in specialized software that control the operation of an overall system, through data operations at client and server computers, network communications, and related processing and messaging functions.

As further discussed herein, the machine learning analysis may be provided on behalf of any number of machine learning algorithms and trained models, including but not limited to deep learning models (also known as deep machine learning, or hierarchical models) that have been trained to perform image recognition tasks, particularly for certain types of medical conditions upon medical images of human anatomy and anatomical representations. As used herein, the term "machine learning" is used to refer to the various classes of artificial intelligence algorithms and algorithm-driven approaches that are capable of performing machine-driven (e.g., computer-aided) identification of trained structures, with the term "deep learning" referring to a multiple-level operation of such machine learning algorithms using multiple levels of representation and abstraction. However, it will be apparent that the role of the machine learning algorithms that are applied, used, and configured in the presently described medical imaging workflow and analysis activities may be supplemented or substituted by any number of other algorithm-based approaches, including variations of artificial neural networks, learning-capable algorithms, trainable object classifications, and other artificial intelligence processing techniques.

In some of the following examples, reference is made to radiology medical imaging procedures (e.g., computed tomography (CT), magnetic resonance imaging (MRI), Ultrasound, and X-ray procedures, etc.) and diagnostic evaluation of the images produced from such imaging procedures that would be performed with an image evaluation (e.g., radiology read) by a licensed and credentialed radiologist. It will be understood that the applicability of the presently described techniques and systems will extend to a wide variety of imaging data (and other data representations) produced by various medical procedures and specialties, including those not involving traditional radiology imaging modalities. Such specialties include, but are not limited, to pathology, medical photography, medical data measurements such as electroencephalography (EEG) and electrocardiography (EKG) procedures, cardiology data, neuroscience data, preclinical imaging, and other data collection procedures occurring in connection with telemedicine, telepathology, remote diagnostics, and other applications of medical procedures and medical science. Accordingly, the performance of the data recognition and workflow modification techniques described herein may apply to a variety of medical image data types, settings, and use cases, including captured static images and multi-image (e.g. video) representations.

FIG. 1 provides an illustration of an example medical imaging system configuration 100 (e.g., a radiology imaging configuration), which enables the processing of data from medical imaging procedures according to an example described herein. The medical imaging system configuration 100 may be used for capturing medical image data in one location and for reviewing medical images associated with the data in another location. The medical imaging system configuration 100 may include many geographically separated imaging devices and many image review terminals. The medical imaging system configuration 100, in a radiology setting, may be embodied as a remote teleradiology system connected to a plurality of healthcare locations, as a localized radiology system used in a single hospital, healthcare provider network, or private radiology practice. The medical imaging system configuration 100 may also operate as an information processing network used to process data from respective imaging procedures regardless of the location of an eventual imaging evaluation.

For purposes of illustration, the medical imaging system configuration 100 depicted in FIG. 1 includes an imaging system 104, an imaging order processing system 102, an image review system 106, and a machine learning analysis system 108. The imaging system 104, for example, may include an imaging device 120, such as a CT scanner, a MRI scanner, or another imaging system (e.g., a radiology imaging modality). Using an energy source such as x-rays or magnetic fields, for example, the imaging device 120 may capture image data. associated with a subject 122 (e.g., a patient).

The imaging device 120 may be controlled by a technician 126 at the medical facility through the use of a workstation terminal or other electronic input control 124. Prior to the technician 126 conducting the imaging procedure for a patient, information may be entered into the electronic input control 124. Information from an electronic medical record (EMR) or healthcare information system (HIS) may also be accessed or updated for the imaging procedure. Relevant information and metadata for the imaging procedure may be placed within the image data itself, or within another data store for further access and processing. For example, the imaging device 120 may produce radiological images generally consistent with the Digital Imaging and Communications in Medicine (DICOM) format, other industry-accepted standards, or proprietary standards.

Consistent with the appropriate image format, the images produced by the image data source may include metadata. This metadata may be generated by the imaging device 120, from input collected by the electronic input control 124, or from input from a HIS or EMR. Further, a series of images produced by the image data source may be obtained directly by the imaging device 120 in the facility shown in FIG. 1, or may be transferred in whole or in part from another image capturing device connected to the imaging device 120 or the medical facility's local network. The imaging data source may also include data transmitted through use of a local facility imaging server (not shown), such as a DICOM server or other Picture Archiving and Communication System (PACS). The metadata within each imaging data file may include identification information such as a patient identifier and an identifier of the series of images, in addition to information about the type of imaging modality and the techniques used to obtain the images. Further, for images formatted according to the DICOM standard, data fields such as a unique image identifier, a unique study identifier, the patient's name, and the facility from which the image originates may be included.

The image data generated by the imaging device 120 may include a series of two-dimensional images, with the collection of some identifiable series of images typically referred to as a "study". In some implementations, the image data may be used to produce a three-dimensional model that can be further manipulated and reformatted for generating two-dimensional (or three-dimensional) images. In other implementations, the image data may include three-dimensional models or graphical data generated by the imaging device 120 or intermediate processing systems. Image data captured by the imaging device 120 may be stored and processed by the imaging order processing system 102 or another local or remote imaging device server (e.g., one or more computers with a processor and a memory), and may be provided to other systems and computers in the medical imaging system configuration 100 through network 130 (e.g., an intranet or the Internet).

In some implementations, medical imaging procedure data provided to the imaging order processing system 102 results in data being stored and processed by one or more computers. For example, the imaging order processing system 102 may determine that the medical imaging procedure data is to be forwarded to a particular computer associated with an evaluating user 142 (e.g., a radiologist workstation) at an image review system 106. As shown, image data may be provided by the imaging order processing system 102 through the network 130 to the image review system 106. Additionally, the medical imaging procedure data provided to the imaging order processing system 102 results in the image data or related medical data being processed by the machine learning analysis system 108. This data may be processed by the machine learning analysis system 108 prior to, in parallel with, or at the same time as the provision or assignment of the image data to the image review system 106.

The image review system 106, for example, may include an image display server 144 (e.g., one or more computers with a processor and a memory), a display device 146 (e.g., a monitor), and input devices 148A-148B (e.g., keyboards, computer mice, joysticks, touch interfaces, voice recognition interfaces, and the like). In some implementations, image data may be processed by the image display server 144 and visually presented to the evaluating user 142 as one or more images at the display device 146. Using the input devices 148A-148B, the evaluating user 142 may interact with the presented images, for example, by manipulating one or more user controls included in a graphical user interface presented at the display device 146 in association with the images. For example, the evaluating user 142 may view an image (or a series of related images), and may specify one or more image adjustments, such as zooming, panning, rotating, changing contrast, changing color, changing view angle, changing view depth, changing rendering or reconstruction technique, and the like. By viewing and interacting with presented image data and with the user interface, for example, the evaluating user 142 may indicate, select, confirm, or input a diagnostic finding value related to a radiological imaging procedure performed on the subject 122.

The machine learning analysis system 108, for example, may also include a data processing server 152 (e.g., one or more computers with a processor and a memory). In some implementations, medical imaging procedure data (or images or individual data representations from such data) may be processed by a compiled binary or other software executed with the processor and the memory of the data processing server 152, to perform specialized image recognition operations, among other operations. The binary or other software executed with the data processing server 152 may implement one or more machine learning models (such as a deep learning algorithm) on the medical imaging procedure data, based on the use of model input data 154 and a trained detection algorithm 156. In some examples, the trained detection algorithm 156 may process historical data inputs from the model input data 154 and current data inputs from the medical imaging procedure data at different levels of the model (such as at deeper/multiple levels of the learning algorithm).

In some implementations, data indications are produced by the data processing server 152 of the machine learning analysis system 108 to effect processing and changes for the subsequent workflows and evaluation activities of the medical imaging procedure data. In some implementations, the data processing server 152 may establish descriptors, markings, annotations, or additional metadata for images of the medical imaging procedure data; in other examples, the data processing server 152 may indicate the presence of particular identified conditions, the absence of certain identified conditions, the likelihood/probability/or other certainty score of such identified conditions, and other related outputs from the operation of a recognition algorithm on the medical imaging procedure data.

When the imaging order processing system 102 receives the image, it may process the image with an image server, for further handling in the evaluation workflow. This processing may include compressing or converting the image to a different format using a compressor/converter component. This image server may also operate to extract metadata from each image file in a series of images. For example, the extracted metadata may include header data for the image providing patient information and medical facility (e.g., hospital) information for the facility that sent the image. The image server may then store all or part of the extracted information in a study record that may be correlated with appropriate orders and studies. The imaging order processing system 102 may operate to process related orders or correlate a particular order (and order data) with a particular set of study images (and image data). In some examples, the imaging order processing system 102 operates to perform a lateral and horizontal movement of studies between an onsite facility and a remote/cloud location with a closely orchestrated feed utilizing HL7 (Health Level 7) and DICOM standards.

As discussed herein, the operations occurring at the imaging order processing system 102 and the image review system 106, including the assignment of a particular study to a particular image review system (or the prioritization of a particular study to a particular image review system) may be affected by the outputs from the operation of the recognition algorithm on the medical imaging procedure data. For example, the evaluation priority of a study within a worklist at an image review system 106 may be changed to a high status based on a time-sensitive identified medical condition such as an intracranial hemorrhage, pulmonary embolism, and the like. Likewise, the imaging order processing system 102 may perform additional or substitute study assignments, data transfers, or other processing with the image review system 106 based on a time-sensitive identified medical condition.

Figure 4:
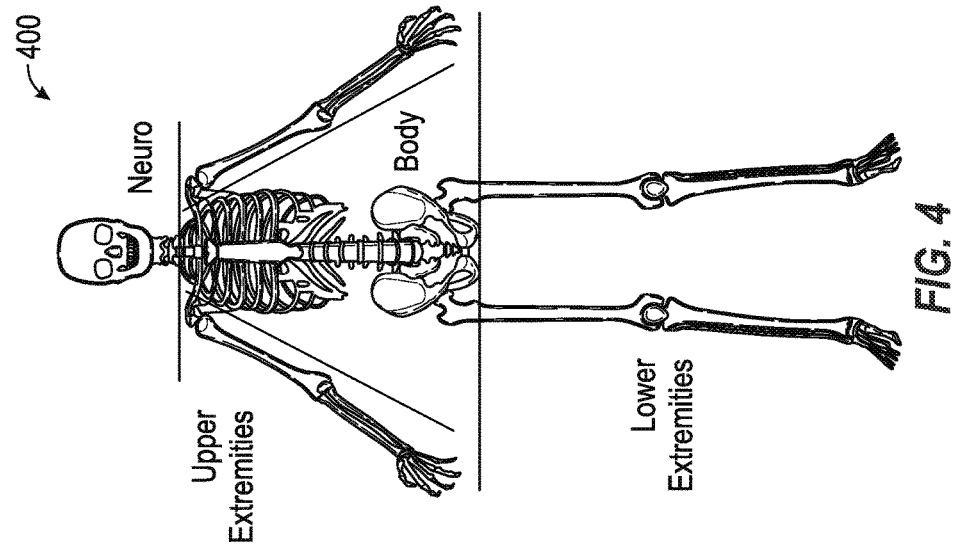
FIG. 4 illustrates a diagram of anatomical areas used for unbundling medical images with a trauma protocol workflow according to an example described herein.
Figure 3:
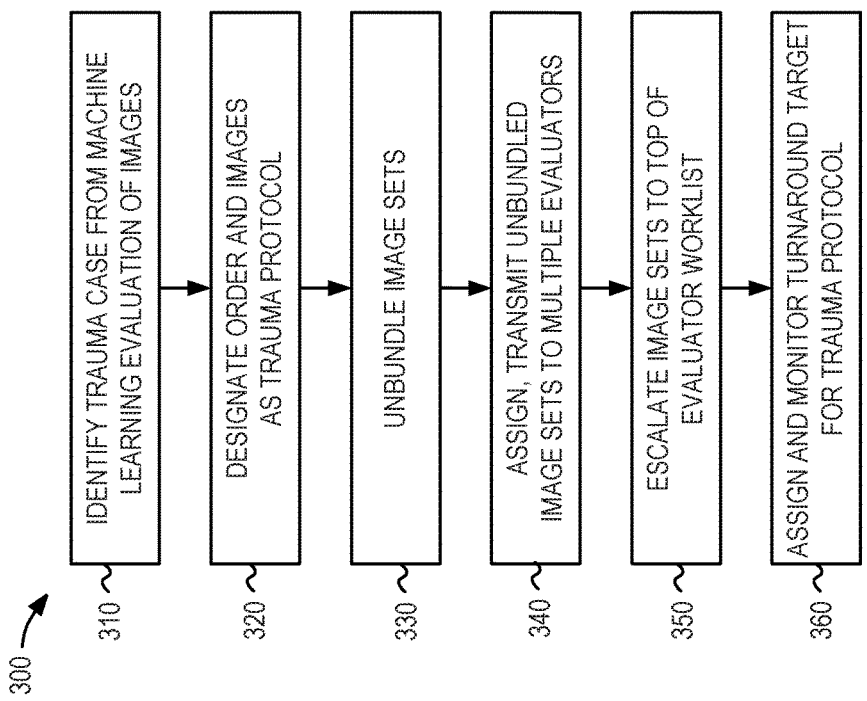
FIG. 3 illustrates a flowchart of operations performed in a trauma protocol workflow for processing medical imaging data according to an example described herein.

In other examples, identified studies with some level of urgency or importance may include additional workflow processing actions that enable assignment to respective image review systems operated by a plurality of evaluators, For example, the identification or detection of a trauma condition may be used to unbundle multiple portions of a study and expedite placement (and evaluation priority) of groups of unbundled images to evaluator worklists. FIGS. 3 and 4 and the associated trauma protocol described below provides examples of a technique to unbundle portions of a study into separate evaluative studies based on regions of anatomy (such as for images captured above the clavicle or another identified body area) to allow multiple evaluators to begin evaluation, and to integrate a combination of the evaluation results back to the requesting medical facility.

Figure 2:
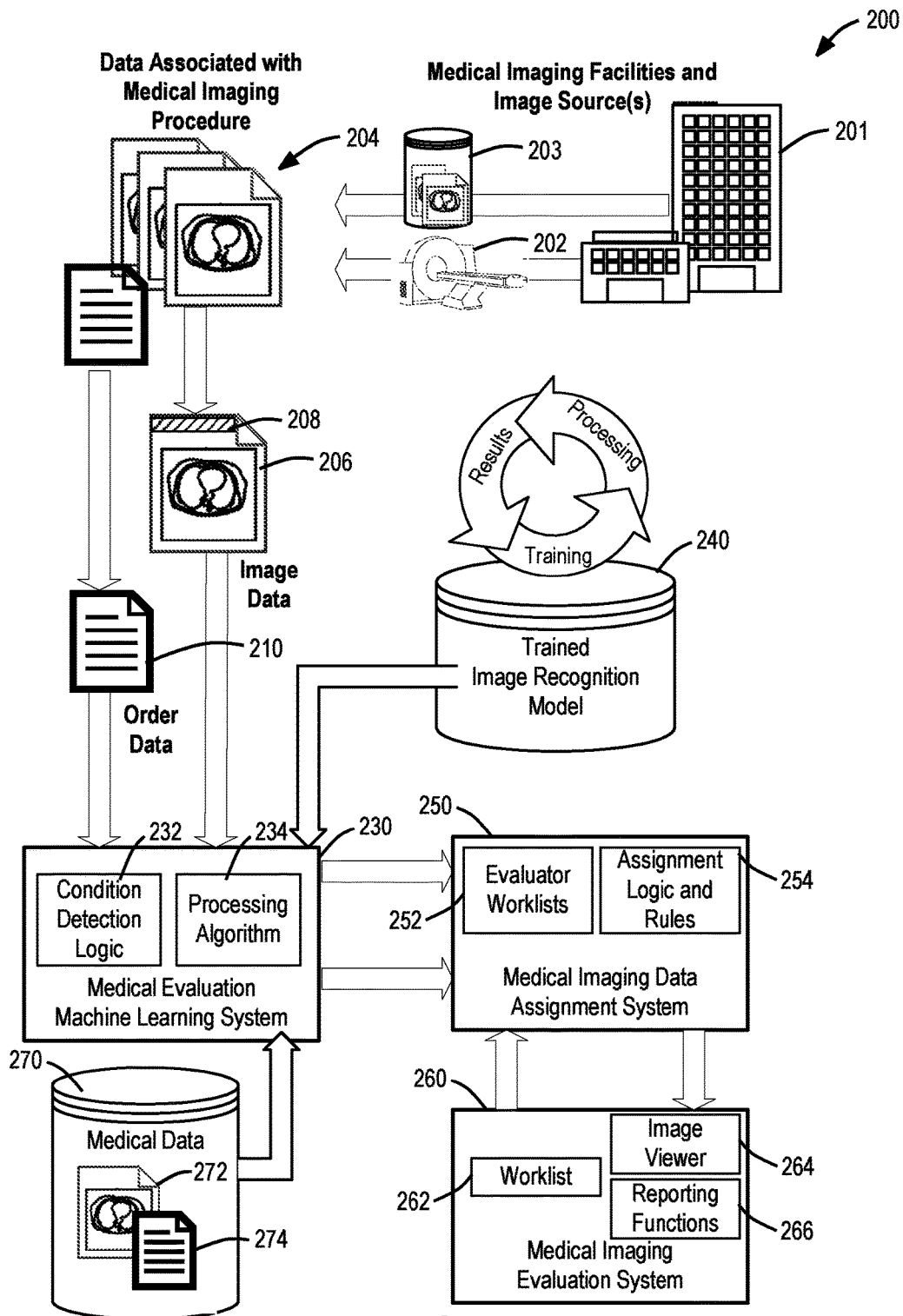
FIG. 2 illustrates system operations in a workflow for analysis of medical imaging data produced from a medical imaging procedure according to an example described herein.

FIG. 2 illustrates a system operations diagram 200 of an example workflow for generating and routing a set of data produced from a particular medical imaging study (e.g., a radiology study) with use of a trained image recognition model 240 applied by a machine learning system 230 according to an example described herein. The system operations diagram 200 is depicted as including image data 206 and order data 210 originating from data of a medical imaging procedure (produced from an imaging modality 202 or a data store 203 at one or more medical imaging facilities 201), with the combination of image data and order data collectively referred to as imaging procedure data 204. It will be understood, however, that the imaging procedure data 204 may also be accompanied, integrated, or associated with information from medical information systems (e.g., EMR data, HIS data, and the like) that is not necessarily produced from the medical imaging procedure.

The system operations diagram 200 illustrates a series of operations executable with an image processing system, such as the medical imaging system configuration 100 or specific components of the imaging order processing system 102 and the machine learning analysis system 108. These operations include the receipt and processing of the imaging procedure data 204 (e.g., radiology study data, including one or both of a radiology order and a radiology imaging data) originating from a particular medical imaging facility or imaging source of the medical imaging facilities 201. This imaging procedure data 204 is processed to obtain identifying data associated with the medical imaging procedure, including an identification of imaging characteristics, type of the imaging procedure, and associated information related to the evaluation of the imaging data. For example, the medical imaging procedure data may include image data 206 and image metadata 208, where the image metadata 208 may include identification information such as a patient identifier and an identifier of the series of images, in addition to information about the type of imaging modality and the techniques used to obtain the images. The imaging procedure data 204 also may include order data 210 for an associated order to perform the diagnostic evaluation of the image data. For example, the order data 210 may be associated with data from an HL7 Order Message (ORM) sent when a healthcare provider requests a service, procedure, or treatment for a patient.

The imaging procedure data 204 may be provided to or assigned within the machine learning system 230 for further use and processing of the image data 206 and the order data 210. For example, the machine learning system 230 may implement automated image recognition through a trained image recognition model 240 with use of a processing algorithm 234 and other condition detection logic 232. Additionally, the condition detection logic 232 may select certain processing algorithms or image recognition models based on the characteristics of the medical imaging procedure indicated by order data 210 or image metadata 208. As one example, an image recognition model relevant to analysis of a medical condition within a human heart may be only applied to certain types of images captured from a patient's abdomen as indicated by the image metadata 208, whereas such an image recognition models would not be applied to images captured from outside a patient's abdomen. As another example, the condition detection logic 232 may perform a review of certain conditions based on the type of preliminary medical inquiries, known conditions, or findings indicated within the information of the order data 210.

In some examples, distinct processing algorithms and trained image recognition processing may be used to detect the characteristics of respective medical conditions; in other examples, a common model or series of algorithms may be used to detect or measure the likelihood one or multiple of many identifiable medical conditions. In some scenarios, additional medical data 270 (e.g., data separate from the particular medical imaging procedure), such as information from a patient's medical history or records, previous imaging evaluations (such as prior images in medical image data 272 and reports in medical report data 274), may be evaluated by the machine learning system 230 to further improve the accuracy and operation of the processing algorithm 234.

The machine learning system 230 may be used to generate an indication of one or more medical conditions detected from image data, and generate associated details and launch processing activities for such medical conditions. The details for such medical conditions may include a confidence level for the presence of certain conditions (e.g., a score that corresponds to a level of recognition of whether certain conditions are detected), identification of specific features or areas in the image in which certain conditions are detected or likely to occur, identification of images in the study in which certain conditions are detected or likely to occur, and similar identifications and indications.

The trained image recognition model 240, for example, may be embodied by a computer-generated deep learning model trained by numerous historical studies and expert results. These studies and results may include the same format and content as the medical imaging study to be evaluated, or may take a derivative form. The training of the trained image recognition model 240 thus may be provided as a result of earlier evaluation actions at the evaluation system 260, or other human created or verified results from prior workflow activities. With use of the trained image recognition model 240, the machine learning system 230 is able to produce accurate and detailed results of machine detected objects through a data-driven cycle of training, processing, and expert verification of results.

Results data from the evaluation of images of the particular study with the machine learning system 230 may be provided to a data assignment system 250, with such results data used for purposes of affecting an assignment or evaluation of the study at one or more selected evaluators. For example, the study and its associated data may be assigned to one or more selected evaluators for diagnostic interpretation, analysis, or other human evaluation of the image data 206, with the results data from the machine learning system 230 used to modify evaluation activities or outputs. Additionally, based on the detection or designation of a severe medical condition (such as a trauma designation), portions of the study may be unbundled and divided up for designation, processing, and transmission to computing systems associated with a plurality of selected evaluators.

The data assignment system 250 also may maintain a series of evaluator worklists 252 that are used to propagate the assignment of studies to respective evaluators, with the evaluator worklists 252 and accompanying graphical user interface outputs being affected (e.g., reordered and adjusted) by the results data from the machine learning system 230. The data assignment system 250 also may use a set of assignment logic and rules 254 to determine the appropriate assignment of studies to the respective evaluators, which may be affected by the results data from the machine learning system 230. For example, a serious and time-sensitive medical condition identified by the machine learning system 230 in a study may result in the study (and its associated data operations and processes) being escalated, prioritized, unbundled, or alerted within multiple of the evaluator worklists 252, to reduce the amount of time it takes for at least one evaluator to begin evaluation of the study in a timely manner.

Further, the data assignment system 250 can operate to provide imaging data to an evaluation system 260 operated by a respective evaluator. The evaluation system 260 may include a worklist 262 of assigned studies to review by a particular evaluating user; an image viewer 264 to output and control the display of various images from the image data; and reporting functions 266 to collect and compile a diagnostic report for medical findings from the image data. The results data provided from the machine learning system 230 may be used to modify the order, orientation, hanging, or positioning of particular images, series, or comparison studies (for example, to most quickly indicate or display images including significant medical findings). These modifications may be implemented in a display or graphical user interface automatically, or in response to user selection (e.g., in response to alerts and user-selectable options in a graphical user interface that can quickly implement the modifications).

Although not expressly depicted within FIG. 2, other data flows may be established or updated between the machine learning system 230 and other components of the data assignment system 250 and evaluation system 260. These data flows may propagate information relating to image annotations, preliminary image findings and report data, order data modifications, and the like, and data values for these fields of information may be implemented in connection with the image viewer 264 or other aspects of the assignment logic and rules 254 or the reporting functions 266. Additionally, the operations performed in connection within FIG. 2 may be implemented with features of a Picture Archiving Communication System (PACS) or Radiology Information System (RIS), features of a HIS or data informatics system, or other components of a medical image procedure management system. In other examples, the data from the machine learning system may be communicated or propagated throughout the system in the system operations diagram 200 to facilities and other users as part of display preferences, report data, or other relevant data indications.

The prioritization of a study in the evaluator worklists 252 is merely one example of operations that may occur in a workflow which are driven by the detection of a medical condition. Other examples of modifications to the workflow may include the implementation of a trauma protocol that operates to unbundle and distribute image series or sets of images from multiple anatomical locations to multiple evaluators. Other examples of modifications to the workflow may include prioritization and other processing activities to certain specialists within a stroke or cardiac condition workflow or like workflows tailored for time-sensitive (or specialized) medical conditions.

FIG. 3 illustrates flowchart 300 of operations performed in a trauma protocol workflow for processing medical imaging data according to an example described herein. As shown, the example flowchart 300 may be used for implementing a trauma protocol that may be used in response to identification of a particular urgency (e.g., either from trauma identified by a referring medical facility or as part of image recognition in a deep learning workflow). For example, a study may be identified as trauma by a referring medical facility according to operational procedures or a medical criterion. Trauma cases may be automatically "unbundled" and assigned to multiple radiologists to read concurrently for faster results, as described in the following examples.

In an example, the assigning an urgency of trauma protocol may be provided based on the identification of a trauma condition in a study from a machine-learning based evaluation of one or more images of the study (operation 310). In response to the identification of the trauma condition, the order (e.g., radiology read order) and any associated images (e.g., radiology images) may be designated in a computer system as under a trauma protocol (operation 320).

With the application of the trauma protocol, an assignment workflow may operate to automatically "unbundle" images in a study (or in associated studies) that include multiple body parts (operation 330). Based on the results of the unbundling, and the identified sets of unbundled images, the portions of the study (and the accompanying sets of images) can be assigned and transmitted to multiple radiologists to be read and evaluated concurrently, simultaneously, or in an expedited manner (operation 340).

Additionally, in response to designating the study as a trauma protocol, the study may be escalated to the top of one or more evaluator worklists (operation 350). The evaluators may be instructed, prompted, and guided to treat trauma protocol cases with a same level of urgency and turnaround time commitments as are applied for other time-sensitive protocols, such as a stroke protocol. For example, a turnaround time target may be assigned and monitored for respective evaluators (operation 360), with re-assignment or alerts being implemented if this turnaround time target (e.g., 20 minutes) is not met.

In further examples, the trauma protocol may be used to generate a call or other electronic communication to a referring or requesting medical facility of critical findings. For example, call priority may be placed on providing results for Head/Cervical Spine studies in connection with the trauma protocol designation. In further examples, this call or electronic communication is configurable to enable receipt of phone call or other electronic communication which includes information on all negative and positive findings for the study.

FIG. 4 illustrates a diagram of anatomical areas 400 used for unbundling medical images with a trauma protocol workflow according to an example described herein. As discussed above, the application of the trauma protocol may automatically "unbundle" cases that include multiple body parts and send them to multiple radiologists to be read concurrently for multiple body regions. The images that are identified from disparate body regions may correspond to the listing of images in body regions (e.g., depicted in the diagram of anatomical areas 400), based on the following classifications: Neuro: head, face, orbits, cervical spine, and neck, areas above the clavicle; Body: chest abdomen and pelvis, thoracic and lumbar spine; Lower extremities: feet, legs; Upper extremities: arms, hands.

Figure 5:
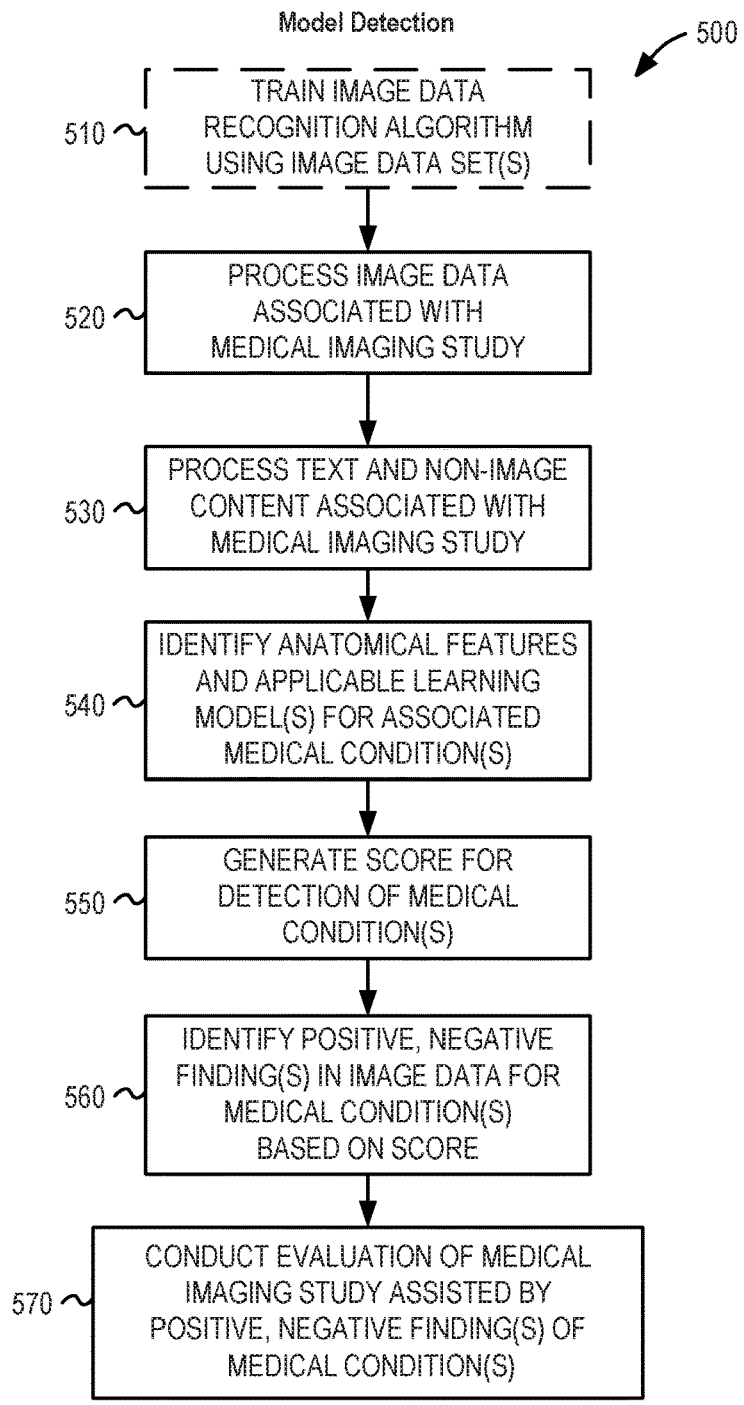
FIG. 5 illustrates a flowchart of a process for detecting a medical condition from image data in a machine learning image analysis workflow according to an example described herein.

FIG. 5 illustrates a flowchart 500 of a process for detecting a medical condition from image data in a machine learning image analysis workflow, which may be performed in an image data processing system such as the systems depicted in FIGS. 1 and 2, according to an example described herein. This process may be initiated through the receipt of a request for a medical imaging evaluation from a medical facility, for example, at a radiology practice or at a teleradiology provider. In other examples, portions of this preparation and assignment process may be initiated as a standalone process, such as may be performed by a third party vendor to validate or evaluate imaging procedure data. Further, aspects of the process may be performed at the medical facility performing the medical imaging procedure (such as with trained image detection processing logic integrated into an intermediate image data store or image modality).

In the flowchart 500, various operations are performed to conduct the detection of conditions within a workflow using a trained image recognition model, such as a trained deep learning algorithm. The workflow operations are commenced with the training of the image data algorithm of the machine learning model (operation 510), such as with use of image data sets, report data, and other data inputs for training a deep learning model. The results of the training may provide a binary or algorithm state that can be re-used (and re-deployed) for analysis of a plurality of subsequent studies, images, and workflow operations.

The operations of the workflow continue with the processing of the imaging data associated with a medical imaging study (operation 520). This processing may involve image extraction, conversion, or transformation operations, in order to obtain input image data for evaluation with the trained image data recognition algorithm. The processing of the imaging data, for example, may involve the operations needed to begin image recognition upon one or multiple images from one or multiple series of a medical imaging study.

The operations of the flowchart 500 continue with the processing of text and other non-image content associated with the medical imaging study (operation 530). The trained image data recognition algorithm may evaluate the text and non-image content at lower levels of the deep learning algorithm, for example, to help influence (and direct) the detection of particular image features and medical conditions in respective images of a study. Using the image and non-image data associated with the medical imaging study, the trained image data recognition algorithm operates to identify anatomical features and applicable learning models that are suitable for the particular image (operation 540). For example, different image recognition models may be more suited to different anatomical features or imaged areas, and the application of the most applicable learning models can be used to detect the most likely or common medical conditions for those anatomical features or imaged areas (and, correspondingly, to exclude attempts to detect medical conditions that are not applicable to certain types of images, imaging scans, and the like).

After performance of the identification and the tailoring of the algorithm to the input data, the trained image data recognition model is utilized to generate a score e.g., confidence score), ranking, or other metric of detected medical conditions within the imaging data (operation 550). Based on this score, ranking, or other metric of detected medical conditions, a set of positive or negative findings for certain medical conditions may be determined (operation 560). For example, a set of positive findings for the occurrence of a pulmonary embolism within images of a patient's lungs may correspond to output characteristics that indicate of the likelihood of an embolism being present within multiple images, the areas of the images in which the embolism has been detected, measurements of the images relating to the condition such as the size of the embolism within specific images, correlation to other reported or detected medical conditions that may indicate a presence of the embolism, and the like.

Finally, the workflow concludes by the performance of the study evaluation (operation 570) by a human evaluator using a computerized evaluation system (e.g., image viewing workstation). The performance of this evaluation, and other activities to assign or process this evaluation, is assisted by the positive or negative findings of the machine learning-identified medical condition. The report or data results from the model then may be communicated to the original ordering medical facility, provided to an evaluator computing system for further review and confirmation, or stored in a results medical information database. Additional information on the evaluation actions for the imaging study, within the context of evaluator activities in an evaluator user interface, are further described below with reference to FIG. 8.

Figure 6:
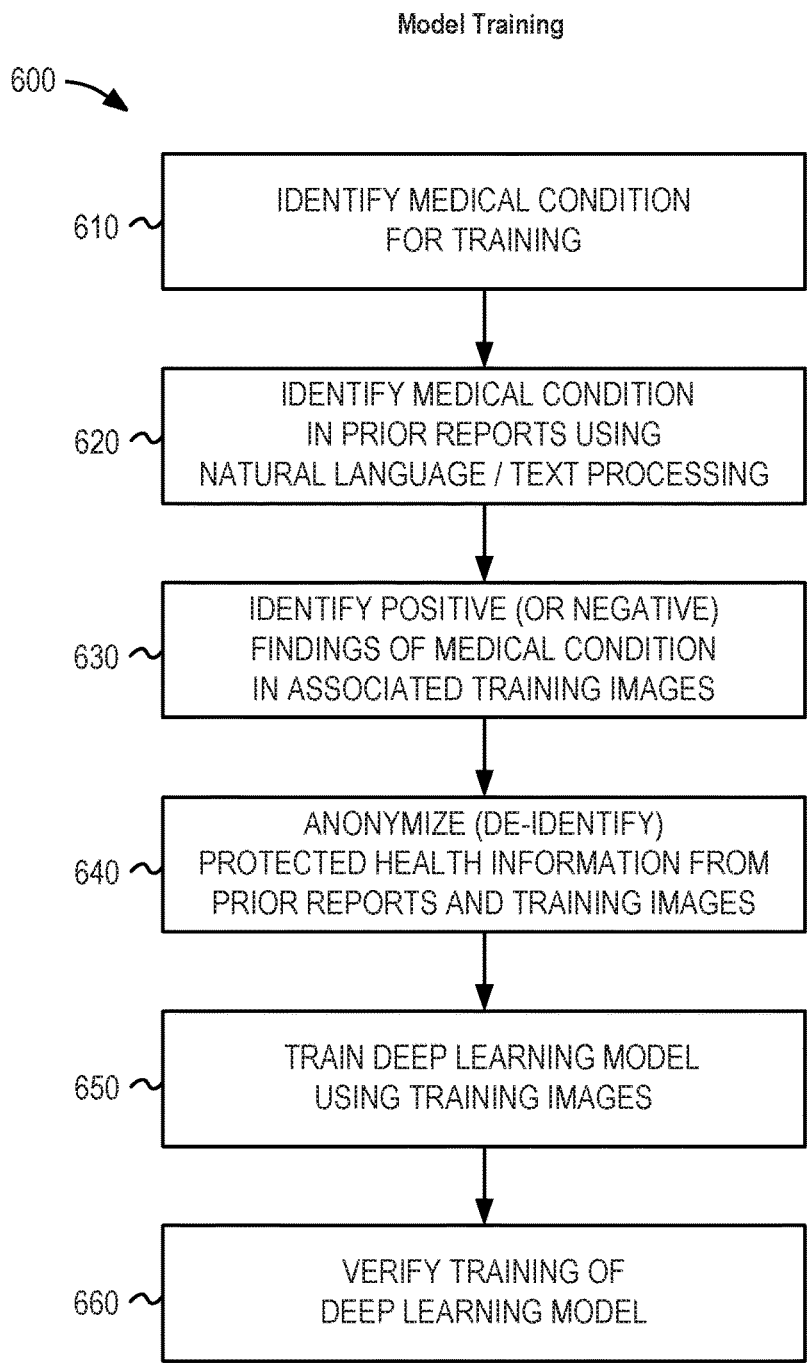
FIG. 6 illustrates a flowchart of a process for training an algorithm used in detecting a medical condition from image data in a machine learning image analysis workflow according to an example described herein.

FIG. 6 illustrates a flowchart 600 of a process for training an algorithm used in detecting a medical condition from image data, such as may be used in training for a deep learning or other machine learning image analysis workflow, according to an example described herein. For example, it will be understood that the training depicted in the flowchart 600 may be used in connection with the training operation (e.g., operation 510) described within the process of FIG. 5.

As shown in the flowchart 600, the process for training may include: identifying a particular medical condition for training (operation 610), which may involve an automated or human-guided selection of a particular medical condition based on frequency/occurrence, severity or urgency, identification ability, or like factors of relevance and usability. The occurrence of this particular medical condition may be identified in prior reports or diagnostic information, such as with use of natural language processing, text keyword matching, or semantic meaning (operation 620), to determine studies (and training images) in which the medical condition occurs (or does not occur). These studies are then further processed to identify positive or negative findings of the particular medical condition (operation 630) in the associated training images.

In connection with the identification, further operations may be performed to anonymize or de-identify protected health information (or other identifying data fields) for use in the training model (operation 640). For example, this may include the anonymization or removal of patient names, medical record numbers, or other identifying characteristics from the training images and associated reports or order data. In some examples, protected health information and other identifying information that is included directly within ("burned-in") pixel data may be detected with the use of optical character recognition (OCR) or other computer-assisted techniques.

Based on the identification of training data from relevant studies and images (and medical condition findings for such images), a deep learning model, or other trainable machine learning algorithm, may be trained (operation 650). This training may include various activities to train multiple layers of the deep learning model, through correlations, statistical modeling, and supervisions as applicable. Additional operations may occur with use of the trained deep learning model to verify training results and assessment accuracy (operation 660), with such verifications potentially occurring during the training process or as adjustments subsequent to detection operations.

It will be understood that variations to the above-described training model may occur based on the pathologies, conditions, and cases to detect within images that can be considered as critical, hard-to-detect, or abnormal. Further, the training of the model may involve various operations to search and analyze report data (and find most representative images) based on criticality, urgency, image clarity, portrayal, or like characteristics.

Figure 7:
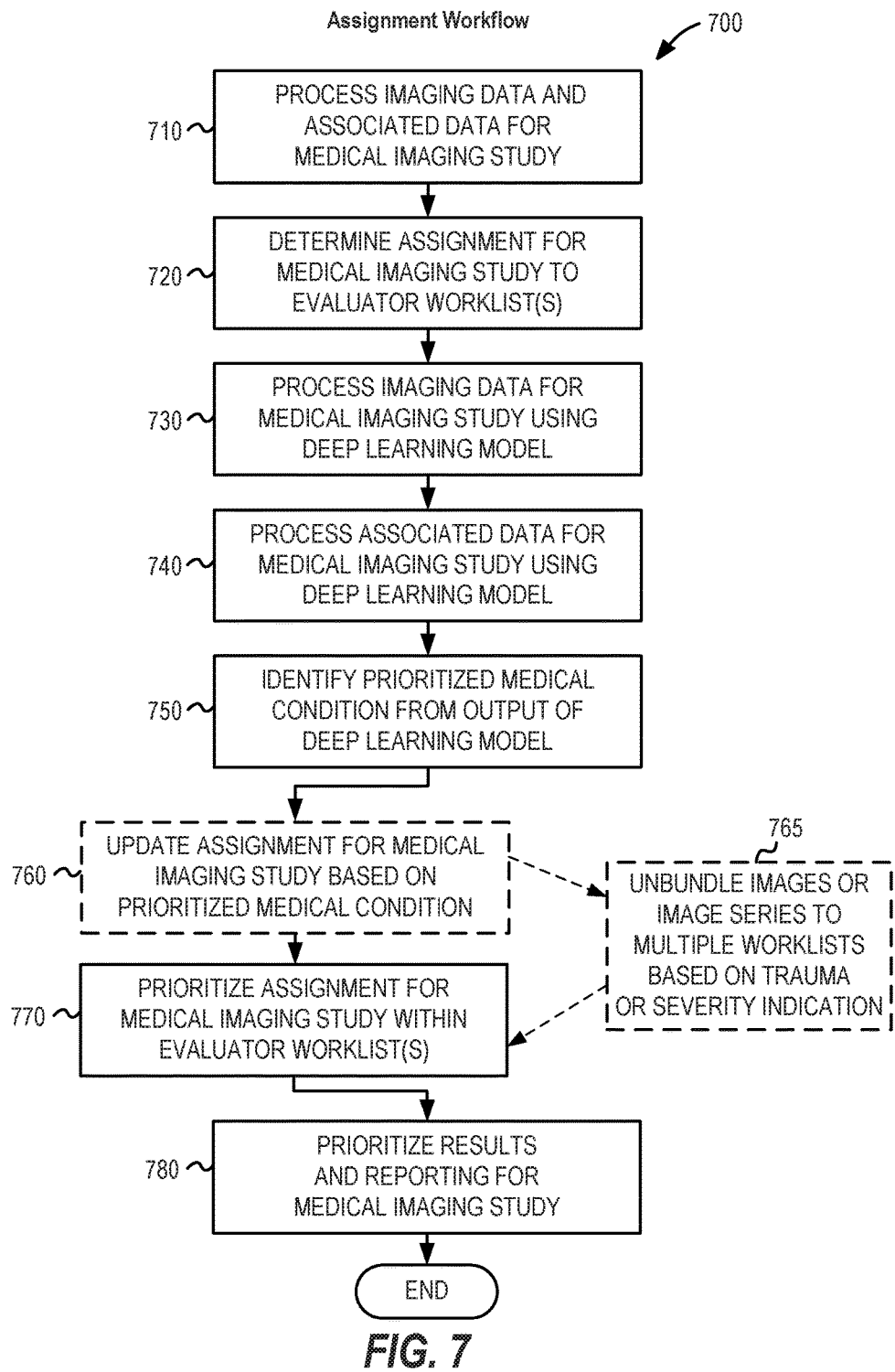
FIG. 7 illustrates a flowchart of example workflow operations performed for processing data of a medical study using results from a machine learning analysis according to an example described herein.

FIG. 7 illustrates a flowchart 700 of an example workflow for processing data of a medical study, based on results from a machine learning analysis according to an example described herein. The particular sequence depicted in the flowchart 700 is illustrated to emphasize assignment actions which may occur in image processing and evaluation activities, such as for a workflow responsible for processing of radiology images and orders. However, it will be understood that the sequence of operations may vary depending on the precise data operations to be performed upon the study data produced by the imaging procedure and the originating medical facility, the conditions present when evaluating the study data, the state of the study data (including the number of errors in the study data), and human actions used to effect the workflow.

The operations depicted in the flowchart 700 include the processing of data associated with a medical imaging study (e.g., processing of image data and associated metadata or order data originating from a medical imaging procedure) (operation 710). This data may be processed, for example, to determine the particular characteristics and type of the imaging procedure, and requirements or conditions for machine evaluation of the procedure. Based on identified information from the study data, the workflow may determine an initial assignment of the medical imaging study to one or more evaluator worklists (operation 720). Caching and pre-loading of imaging data to respective evaluators may follow such assignments or assignment revisions.

The workflow further includes processing the imaging data for the medical imaging study using a deep learning model (operation 730), or other trained machine image recognition algorithm. For example, processing the imaging data may include performing image recognition for one or more medical conditions, identifiable objects, or machine-detectable scenarios. The workflow may further include processing non-image data associated with the medical imaging study using the deep learning model (operation 740) or an evaluative algorithm related to the image recognition model. For example, non-image data which indicates certain parameters of the medical imaging procedure may be provided as an input to lower levels of the deep learning algorithm. This non-image data may be processed with use of natural language processing, keyword detection, or like analysis, upon metadata, clinical history and reports, request or order data, and other machine-readable information.

As a result of the deep learning algorithm, various indications of a medical condition may be produced. This may include the identification of a prioritized (e.g., time-sensitive) medical condition (operation 750). In some examples, the identification of the medical condition may be tied or correlated to clinical history or forms of non-imaging data. As a result of the identification of the medical condition, an updated assignment in the workflow may be implemented (operation 760), for example, to additional or other medical evaluators, such as based on the medical specialization of evaluators who would be best qualified for a medical evaluation of the identified condition. (It will be understood, however, that the assignment occurring in operations 720 and 760 may be reordered to occur after conducting processing of the image data in the deep learning model.) In some examples, based on a trauma or severity indication (e.g., provided in the order data or detected by the deep learning model), images or image series may be unbundled or divided among multiple worklists and evaluators (operation 765). A further example of an application of a trauma protocol with use of a trauma indication and the unbundling of images into multiple body regions is depicted in FIGS. 3 and 4.

As a result of the identification of the prioritized medical condition, various actions may occur to assist the evaluator worklist with data-driven activities. These may include the prioritization of the assignment within one or more evaluator worklists by the evaluating user (operation 770), and the prioritization of results and reporting for the medical imaging study from the evaluating user back to the requesting medical facility (operation 780).

Other workflow actions consistent with the use cases described herein may also be implemented. For example, with use of natural language processing (NLP) of clinical history and order information (e.g., in the evaluation of non-image data in operation 740), false positives and previously known findings may be identified but excluded from study prioritization. Likewise, these and other types of non-image data might be used in training the model, or in excluding or redirecting the results of the model at lower levels of a deep learning model.

Figure 8:
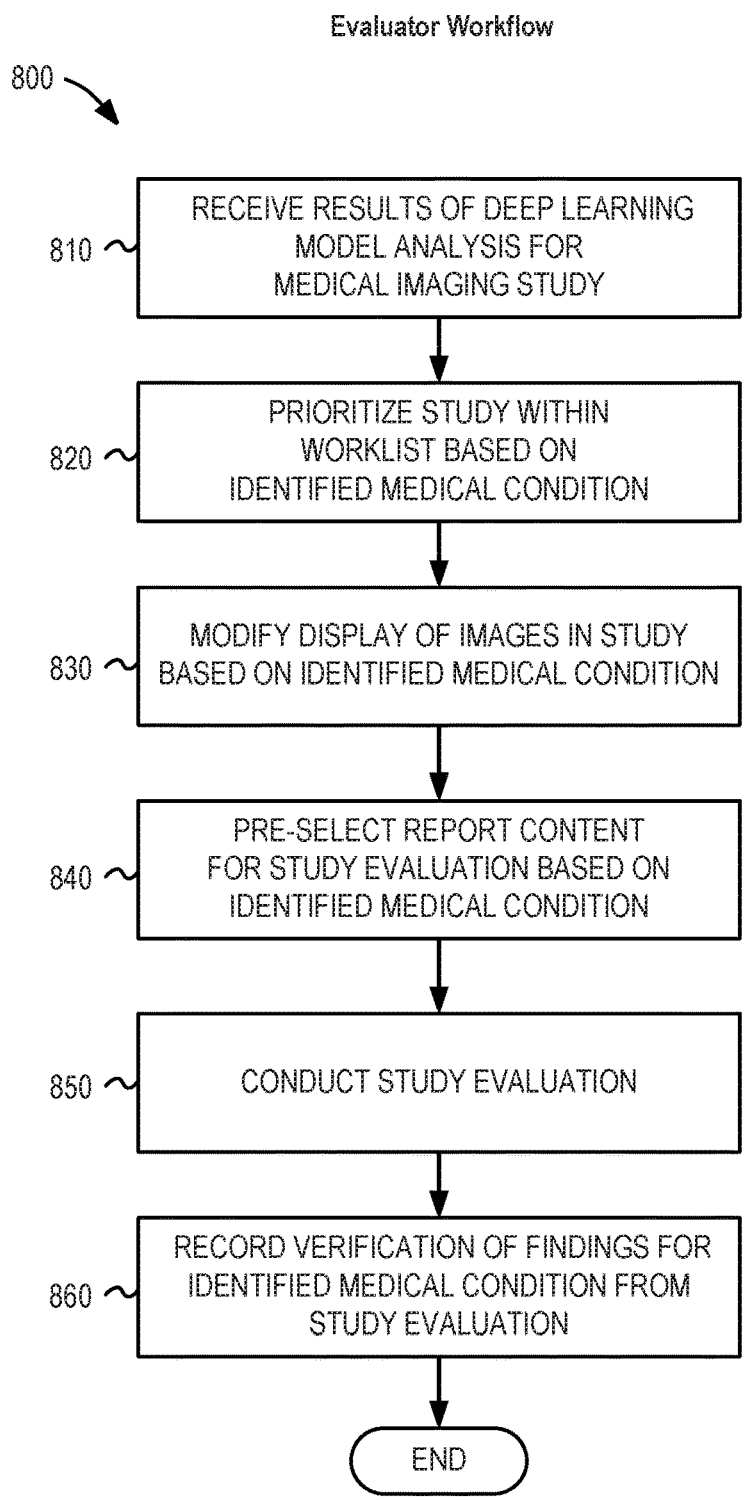
FIG. 8 illustrates a flowchart of additional workflow operations performed for processing data of a medical study using results from a machine learning analysis according to an example described herein.

FIG. 8 provides an illustration of a flowchart 800 of additional workflow operations that may be performed upon a particular imaging study (and associated imaging data) at an evaluator computing workstation, or for performance assisted by an evaluator, based on the medical condition identification scenarios described herein. For example, these workflow operations may be implemented in portions of a viewer, reporting, or other evaluative graphical user interface and associated computer system processes.

As illustrated, the various operations of flowchart 800 may include processing operations that are performed to accomplish evaluation that is assisted by the results of the machine learning algorithm (specifically, a deep learning model analysis). For example, the operations may include: receiving results of the deep learning model analysis for the particular medical imaging study (operation 810), which may include an indication (or a non-indication) of a specific medical condition, a relevance/likelihood/confidence score of the specific medical condition, identified findings of the specific medical condition, and the like. Based on the indication and associated workflow modifications, the study may be prioritized within the worklist of the evaluator (operation 820), such as to receive a higher location, highlight, or alert in a worklist graphical user interface.

Based on the prioritization and the indication of the identified medical condition, various operations may occur within the graphical user interface of the evaluating user to modify the display of the study (operation 830). The changes to the display of the study may include providing computer-generated modifications, groupings, annotations, or modified arrangement of the display of the images. Additionally, operations to assist the evaluation of the study based on the specific condition may be implemented in an evaluation graphical user interface, such as the pre-selection of report content (operation 840).

The workflow of flowchart 800 concludes with the performance of the study evaluation through human and machine operations (operation 850) through a combination of evaluator and automated processing actions, and the tracking of verification of findings from the performance of the study evaluation (operation 860) to store and capture data produced as a result of the evaluator. For example, an evaluator may verify that the medical condition was correctly (or incorrectly) detected by the machine learning model, or provide feedback and condition state modification for report generation purposes and further model training. In further examples, an evaluator may designate a particular condition for training, educational, or further review purposes (such as to designate a particular detected condition within an image as an unambiguous and clear state of a certain medical condition).

The presently described prioritization and indications of the identified medical condition may assist with other aspects of the evaluation and reporting activities. For example, a computer-aided location or annotation of an anatomical feature (or a medical condition finding) may be designated by the machine learning model for display within an evaluation image viewer interface. As another example, a computer-determined preferred phrasing or textual output may be designated by the machine learning model for use in a reporting interface. As another example, key images which indicate the medical condition may be designated by the machine learning model for use in an evaluation image viewer interface or in an electronic version of a report. Other variations may occur that identify images of importance and modify a presentation state based on results of the machine learning model.

Other variations or additional actions for the previously described workflow may be performed using the results of the machine learning model. For example, triggering a phone notification workflow based upon the image analysis results. With an internal head bleed that is detected by the machine learning model, the phone call could be initiated before a radiologist has even opened the study on his or her workstation in order to reduce the amount time it takes to contact the referring physician. When the call connects, the radiologist could access and review the images in real-time (if he or she hasn't read them yet) and provide a confirmation of the head bleed from the respective images. Similar alerts, graphical user interface actions, and electronic functions may be performed in a workflow based on such results of the machine learning model.

Figure 9:
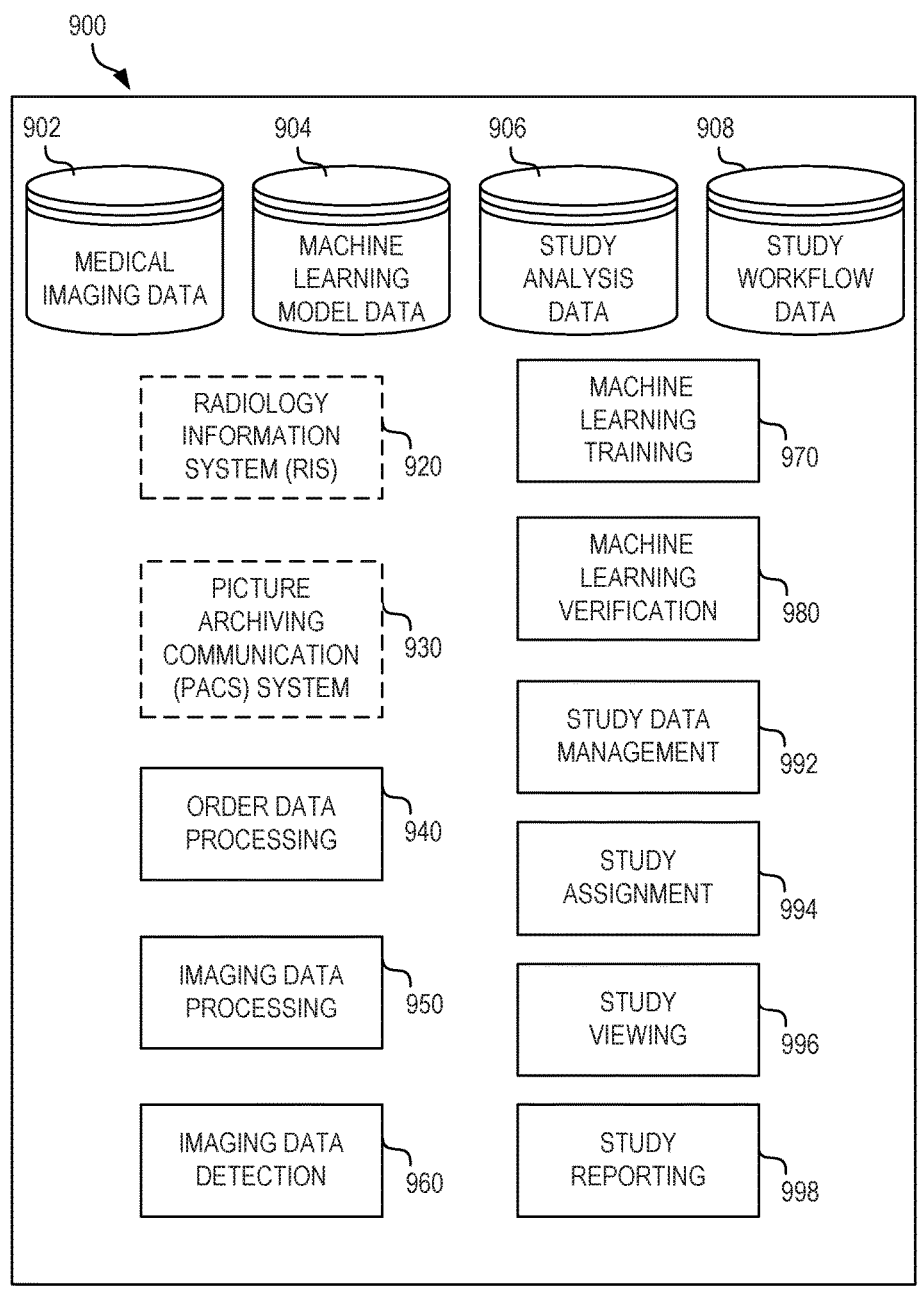
FIG. 9 illustrates a system configuration of a medical imaging data processing system arranged to process medical imaging data with machine learning operations according to an example described herein.

FIG. 9 illustrates an example configuration of a system architecture 900 configured to implement the presently described processing system according to an example described herein. System architecture 900 may implement components such as the imaging order processing system 102 and features of the image review system 106 and the machine learning analysis system 108. The system architecture 900 may include features of a radiology information system 920, a picture archiving communication system 930, order data processing 940, image data processing 950, image data detection 960, machine learning training 970, machine learning verification 980, study data management 992, study assignment 994, study viewing 996, and study reporting 998. In operation with these features, the system architecture 900 may further include a plurality of databases or data stores, including a medical imaging database 902, a machine learning model database 904, a study analysis database 906, and a study workflow database 908. Such features may be embodied by any number of software or hardware forms (including through the use of physical or logical blocks of computer instructions, which may, for instance, be organized as an object, procedure, or function).

The medical imaging database 902 may provide a location for storage of imaging data (and metadata) for medical imaging procedures and associated studies. The machine learning model database 904 may provide a location for storage of deep learning models, inputs, and relevant parameters for operation of the machine learning algorithms. The study analysis database 906 may provide a location for storage of information for study evaluation states of particular studies, preferences for study evaluations, and other data fields used to assist the study evaluation in response to the performance of the machine learning models. The study workflow database 908 may provide a location for storage of information for workflow states of particular studies, preferences for workflow operations, and other data fields used to assist the workflow operations occurring in response to the performance of the machine learning models.

The respective features of the system architecture 900 may perform functional operations to effect the processing, image identification, and workflow management techniques described herein. For example, the radiology information system 920 may be used to provide respective information processing functions of a RIS. The picture archiving communication system 930 may be used to provide image storage and access features of a Picture Archiving Communication System (PACS). The order data processing 940 may be used to process orders, and determine relevant information for non-image data of studies. The image data processing 950 may be used to request, receive, validate, and store images data of studies.

The image data processing 950 may be used to perform imaging processing operations on imaging data obtained from a set of data associated with a medical imaging procedure, or from a customer imaging device, an image archive, medical facility data store, or other imaging data source, such as with processing operations that provide image data as input to the machine learning models. The image data detection 960 may be used to implement the machine learning model, such as with performance of a deep learning model to detect certain medical conditions within the images of the study image data.

The machine learning training 970 may be used to implement training of the machine learning model, such as with the use of imaging and non-imaging data completed by previous study evaluations. The machine learning verification 980 may be used to compare results of the image detection operations with results of the study evaluations, and to modify the machine learning model based on verification of outcomes. The study data management 992 may be used to coordinate the transmission and transfer of image and non-image data associated with an imaging study based on the results of the image detection operations and the adjusted workflows. The study assignment 994 may be used to provide assignments to one or more evaluators (and to facilitate the transfer of data to computing systems associated with the one or more evaluators) based on the results of the image detection operations and the adjusted workflows. The study viewing 996 may be used to view studies (and specific types of rendering data) on screen by an evaluating user, which may be influenced by the detection of certain medical conditions, prioritization, or other results of the image detection operations and the adjusted workflows. The study reporting 998 may be used to establish reporting functions for the evaluating user, from report information that is created or contributed to by the evaluating user, with such report information being influenced or assisted by the results of the image detection operations and the adjusted workflows.

Figure 10:
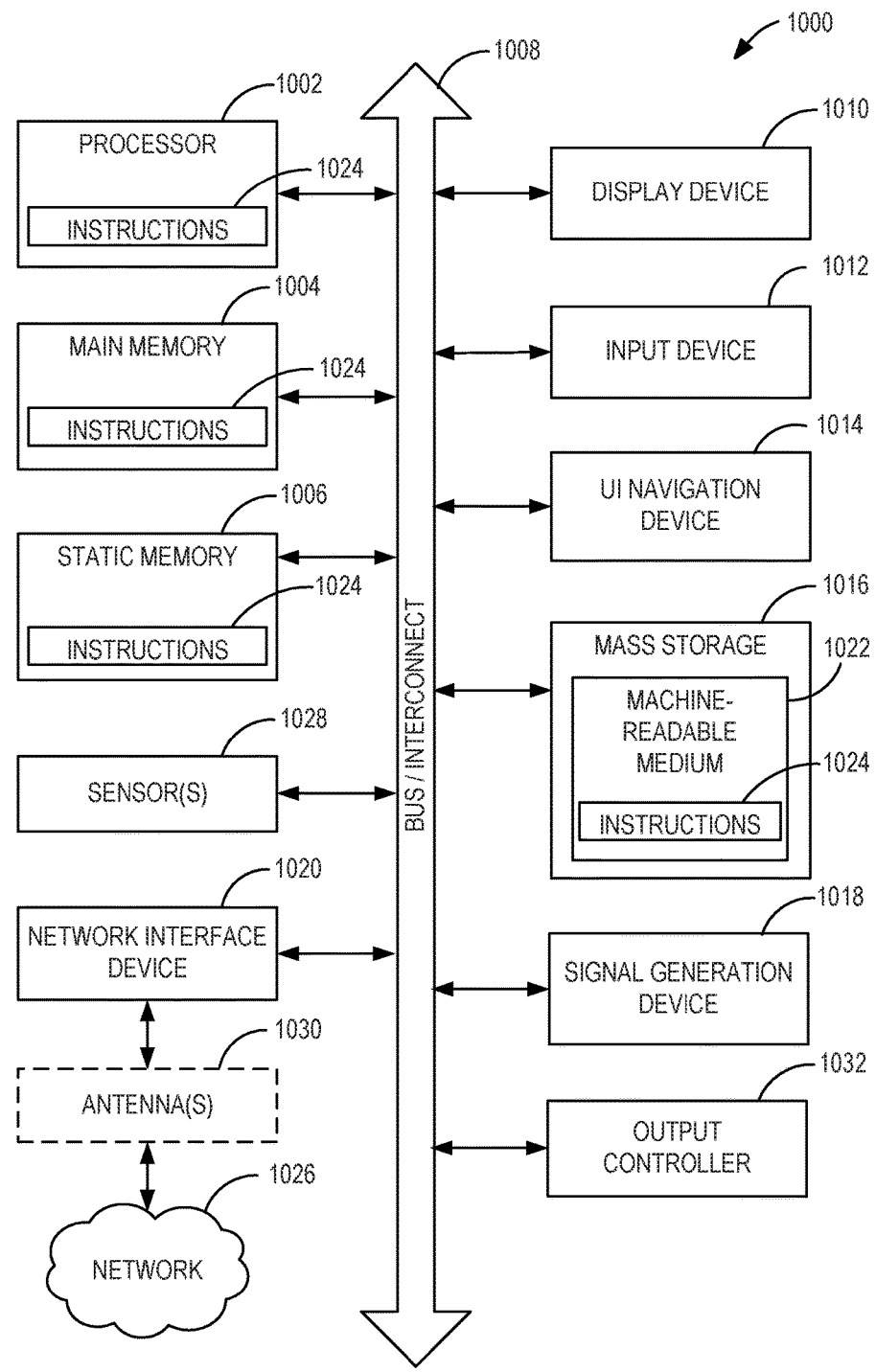
FIG. 10 illustrates an example of a machine configured to perform computing operations according to an example described herein.

FIG. 10 is a block diagram illustrating an example computing system 1000 upon which any one or more of the methodologies herein discussed may be run according to an example described herein. Computer system 1000 may be embodied as a computing device, providing operations of the components featured in the various figures, including components of the imaging order processing system 102, the imaging system 104, the image review system 106, the machine learning analysis system 108, components and data storage elements in system architecture 900, or any other processing or computing platform or component described or referred to herein. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The computer system machine may be a personal computer (PC) that may or may not be portable (e.g., a notebook or a netbook), a tablet, a Personal Digital Assistant (PDA), a mobile telephone or smartphone, a web appliance, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

Example computer system 1000 includes a processor 1002 (e.g., a central processing unit (CPU), a graphics processing unit (GPU) or both), a main memory 1004 and a static memory 1006, which communicate with each other via an interconnect 1008 (e.g., a link, a bus, etc.). The computer system 1000 may further include a video display unit 1010, an alphanumeric input device 1012 (e.g., a keyboard), and a user interface (UI) navigation device 1014 (e.g., a mouse). In one embodiment, the video display unit 1010, input device 1012 and UI navigation device 1014 are a touch screen display. The computer system 1000 may additionally include a storage device 1016 (e.g., a drive unit), a signal generation device 1018 (e.g., a speaker), an output controller 1032, and a network interface device 1020 (which may include or operably communicate with one or more antennas 1030, transceivers, or other wireless communications hardware), and one or more sensors 1028.

The storage device 1016 includes a machine-readable medium 1022 on which is stored one or more sets of data structures and instructions 1024 (e.g., software) embodying or utilized by any one or more of the methodologies or functions described herein. The instructions 1024 may also reside, completely or at least partially, within the main memory 1004, static memory 1006, and/or within the processor 1002 during execution thereof by the computer system 1000, with the main memory 1004, static memory 1006, and the processor 1002 constituting machine-readable media.

While the machine-readable medium 1022 is illustrated in an example embodiment to be a single medium, the term "machine-readable medium" may include a single medium or multiple media (e.g., a centralized or distributed database, and/or associated caches and servers) that store the one or more instructions 1024. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, optical media, and magnetic media. Specific examples of machine-readable media include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 1024 may further be transmitted or received over a communications network 1026 using a transmission medium via the network interface device 1020 utilizing any one of a number of well-known transfer protocols (e.g., HTTP). Examples of communication networks include a local area network (LAN), wide area network (WAN), the Internet, mobile telephone networks, Plain Old Telephone (POTS) networks, and wireless data networks (e.g., Wi-Fi, 3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

Other applicable network configurations may be included within the scope of the presently described communication networks. Although examples were provided with reference to a local area wireless network configuration and a wide area Internet network connection, it will be understood that communications may also be facilitated using any number of personal area networks, LANs, and WANs, using any combination of wired or wireless transmission mediums.

The embodiments described above may be implemented in one or a combination of hardware, firmware, and software. For example, the features in the system architecture 900 of the processing system may be client-operated software or be embodied on a server running an operating system with software running thereon. While some embodiments described herein illustrate only a single machine or device, the terms "system", "machine", or "device" shall also be taken to include any collection of machines or devices that individually or jointly execute a set (or multiple sets) of instructions to perform any one or more of the methodologies discussed herein.

Examples, as described herein, may include, or may operate on, logic or a number of components, modules, features, or mechanisms. Such items are tangible entities (e.g., hardware) capable of performing specified operations and may be configured or arranged in a certain manner. In an example, circuits may be arranged (e.g., internally or with respect to external entities such as other circuits) in a specified manner as a module, component, or feature. In an example, the whole or part of one or more computer systems (e.g., a standalone, client or server computer system) or one or more hardware processors may be configured by firmware or software (e.g., instructions, an application portion, or an application) as an item that operates to perform specified operations. In an example, the software may reside on a machine readable medium. In an example, the software, when executed by underlying hardware, causes the hardware to perform the specified operations.

Accordingly, such modules, components, and features are understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules, components, and features are temporarily configured, each of the items need not be instantiated at any one moment in time. For example, where the modules, components, and features comprise a general-purpose hardware processor configured using software, the general-purpose hardware processor may be configured as respective different items at different times. Software may accordingly configure a hardware processor, for example, to constitute a particular item at one instance of time and to constitute a different item at a different instance of time.

Additional examples of the presently described method, system, and device embodiments are suggested according to the structures and techniques described herein. Other non-limiting examples may be configured to operate separately, or can be combined in any permutation or combination with any one or more of the other examples provided above or throughout the present disclosure.

What is claimed is:

1. A method of electronic processing for data in a medical evaluation workflow, comprising operations performed by processing circuitry of a computing device, the operations comprising:

receiving image data and non-image data associated with a medical imaging study;

determining a potential medical condition to evaluate in the image data, based on information provided in the non-image data;

selecting a deep learning model to perform automated image recognition on the image data, the deep learning model trained to evaluate at least one characteristic of the potential medical condition;

determining a state of the potential medical condition from the image data, using the deep learning model to perform automated feature recognition on the image data; and modifying an electronic workflow for performing a diagnostic evaluation of the medical imaging study, wherein the electronic workflow is modified based on the state of the potential medical condition recognized from the image data.

2. The method of claim 1, wherein determining the state of the potential medical condition, comprises:

generating at least one value that corresponds to a level of feature recognition in the image data for the state of the potential medical condition;

wherein the state of the potential medical condition recognized from the image data indicates a positive finding or a negative finding related to the potential medical condition being detected or not detected in at least one image of the image data.

3. The method of claim 1, wherein the information provided in the non-image data indicates that an anatomical area or anatomical feature is represented in the image data, and wherein the deep learning model is further selected based on the anatomical area or anatomical feature that is represented in the image data.

4. The method of claim 1, wherein modifying the electronic workflow for performing the diagnostic evaluation of the medical imaging study includes:

determining an assignment for the medical imaging study within an evaluator worklist, the evaluator worklist corresponding to a particular computing system;

identifying that the medical imaging study includes an urgent medical condition based on the state of the potential medical condition determined from the image data; and prioritizing the assignment for the medical imaging study in the evaluator worklist.

5. The method of claim 1, the operations further comprising:

determining a first assignment for the medical imaging study within a first evaluator worklist, based on the state of the potential medical condition determined from the image data, wherein the first evaluator worklist corresponds to a first computing system; and determining a second assignment for the medical imaging study within a second evaluator worklist, based on the state of the potential medical condition determined from the image data, wherein the second evaluator worklist corresponds to a second computing system;

wherein the electronic workflow is modified to provide a combination of results for the medical imaging study from the first assignment and the second assignment.

6. The method of claim 1, the operations further comprising:

unbundling a plurality of series of images within the image data based on an indication of a trauma or other time-sensitive medical condition from the state of the potential medical condition, wherein the plurality of series of images are unbundled into respective groupings based on anatomical regions captured by the plurality of series of images;

wherein modifying the electronic workflow for performing the diagnostic evaluation of the medical imaging study includes assigning and prioritizing the respective groupings within the medical imaging study in a first worklist and a second worklist, wherein the first worklist corresponds to a first computing system and wherein the second worklist corresponds to a second computing system.

7. The method of claim 1, the operations further comprising:

receiving results indicated by an evaluating user, the results produced from the diagnostic evaluation of the medical imaging study, and verifying training of the deep learning model based on a comparison of at least one result from the automated image recognition with at least one result produced from the diagnostic evaluation of the medical imaging study produced at least in part by an evaluating user.

8. The method of claim 1, the operations further comprising:

performing a verification of results and accuracy of the diagnostic evaluation of the medical imaging study, based on the state of the potential medical condition determined using the deep learning model.

9. The method of claim 1, the operations further comprising:

receiving results produced from the diagnostic evaluation of the medical imaging study;

verifying accuracy of the automated image recognition with the deep learning model;

wherein further training of the deep learning model is performed based on the accuracy of the automated image recognition with the deep learning model related to the diagnostic evaluation of the medical imaging study.

10. The method of claim 1, wherein modifying the electronic workflow comprises modifying reporting or viewing of the diagnostic evaluation of the medical imaging study, based on the state of the potential medical condition determined using the deep learning model.

11. The method of claim 1, the operations further comprising:

wherein the image data is provided from a radiological imaging procedure, wherein the non-image data is provided from a radiological imaging order, and wherein the medical imaging study corresponds to a radiological read request for diagnostic evaluation of the image data by a medical professional evaluator, the radiological read request indicated by the radiological imaging order.

12. A computing system, comprising:

at least one processor; and at least one memory device including instructions embodied thereon, wherein the instructions, which when executed by the processor, cause the processor to perform operations for processing for data in a medical evaluation workflow, the operations comprising:

extracting image data and non-image data associated with a medical imaging study;

determining a potential medical condition to evaluate in the image data, based on information provided in the non-image data;

selecting a deep learning model to perform automated image recognition on the image data, the deep learning model trained to evaluate at least one characteristic of the potential medical condition;

determining a state of the potential medical condition from image content of the image data, using automated image recognition on the image data with the deep learning model; and modifying an electronic workflow for performing a diagnostic evaluation of the medical imaging study, wherein the electronic workflow is modified based on the state of the potential medical condition recognized from the image data.

13. The computing system of claim 12, wherein determining the state of the potential medical condition, comprises:

generating at least one value that corresponds to a level of feature recognition in the image data for the state of the potential medical condition;

wherein the state of the potential medical condition recognized from the image data indicates a positive finding or a negative finding related to the potential medical condition being detected or not detected in at least one image of the image data.

14. The computing system of claim 12, wherein the information provided in the non-image data indicates that an anatomical area or anatomical feature is represented in the image data, and wherein the deep learning model is further selected based on the anatomical area or anatomical feature represented in the image data.

15. The computing system of claim 12, wherein modifying the electronic workflow for performing the diagnostic evaluation of the medical imaging study includes:

determining an assignment for the medical imaging study within an evaluator worklist, the evaluator worklist corresponding to a particular computing system;

identifying that the medical imaging study includes an urgent medical condition based on the state of the potential medical condition determined from the image data; and prioritizing the assignment for the medical imaging study in the evaluator worklist.

16. The computing system of claim 12, the instructions to further cause operations comprising:

determining a first assignment for the medical imaging study within a first evaluator worklist, based on the state of the potential medical condition determined from the image data, wherein the first evaluator worklist corresponds to a first computing system; and determining a second assignment for the medical imaging study within a second evaluator worklist, based on the state of the potential medical condition determined from the image data, wherein the second evaluator worklist corresponds to a second computing system;

wherein the electronic workflow is modified to provide a combination of results for the medical imaging study from the first assignment and the second assignment.

17. The computing system of claim 12, the instructions to further cause operations comprising:

unbundling a plurality of series of images within the image data based on an indication of a trauma or other time-sensitive medical condition from the state of the potential medical condition, wherein the plurality of series of images are unbundled into respective groupings based on anatomical regions captured by the plurality of series of images;

wherein modifying the electronic workflow for performing the diagnostic evaluation of the medical imaging study includes assigning and prioritizing the respective groupings within the medical imaging study in a first worklist and a second worklist, wherein the first worklist corresponds to a first computing system and wherein the second worklist corresponds to a second computing system.

18. The computing system of claim 12, the instructions to further cause operations comprising:

receiving results indicated by an evaluating user, the results produced from the diagnostic evaluation of the medical imaging study, and verifying training of the deep learning model based on a comparison of at least one result from the automated image recognition with at least one result produced from the diagnostic evaluation of the medical imaging study produced at least in part by an evaluating user.

19. The computing system of claim 12, the instructions to further cause operations comprising:

performing a verification of results and accuracy of the diagnostic evaluation of the medical imaging study, based on the state of the potential medical condition determined using the deep learning model.

20. The computing system of claim 12, the instructions to further cause operations comprising:

receiving results produced from the diagnostic evaluation of the medical imaging study;

verifying accuracy of the automated image recognition with the deep learning model;

wherein further training of the deep learning model is performed based on the accuracy of the automated image recognition with the deep learning model related to the diagnostic evaluation of the medical imaging study.

21. The computing system of claim 12, wherein modifying the electronic workflow comprises modifying reporting or viewing of the diagnostic evaluation of the medical imaging study, based on the state of the potential medical condition determined using the deep learning model.

22. At least one non-transitory machine-readable storage medium, the machine-readable storage medium including instructions that, when executed by processing circuitry of a computing system, causes the processing circuitry to perform operations comprising:

identifying image data and non-image data associated with a medical imaging study;

determining a potential medical condition to evaluate in the image data, based on information provided in the non-image data;

selecting a deep learning model to perform automated image recognition on the image data, the deep learning model trained to evaluate at least one characteristic of the potential medical condition;

determining, a state of the potential medical condition from the image data, using the deep learning model to perform automated feature recognition on the image data; and modifying an electronic workflow for performing a diagnostic evaluation of the medical imaging study, wherein the electronic workflow is modified based on the state of the potential medical condition recognized from the image data.

23. The non-transitory machine-readable storage medium of claim 22, wherein determining the state of the potential medical condition, comprises:

generating at least one value that corresponds to a level of feature recognition in the image data for the state of the potential medical condition;

wherein the state of the potential medical condition recognized from the image data indicates a positive finding or a negative finding related to the potential medical condition being detected or not detected in at least one image of the image data.

24. The non-transitory machine-readable storage medium of claim 22, the operations further comprising:

determining a first assignment for the medical imaging study within a first evaluator worklist, based on the state of the potential medical condition determined from the image data, wherein the first evaluator worklist corresponds to a particular computing system; and determining a second assignment for the medical imaging study within a second evaluator worklist, based on the state of the potential medical condition determined from the image data, wherein the second evaluator worklist corresponds to a second computing system;

wherein the electronic workflow is modified to provide a combination of results for the medical imaging study from the first assignment and the second assignment.

25. The non-transitory machine-readable storage medium of claim 22, the operations further comprising:

receiving results indicated by an evaluating user, the results produced from the diagnostic evaluation of the medical imaging study, and verifying training of the deep learning model based on a comparison of at least one result from the automated image recognition with at least one result produced from the diagnostic evaluation of the medical imaging study produced at least in part by an evaluating user.

* * * * *